US009283252B2

(12) United States Patent
Ochi et al.

(10) Patent No.: US 9,283,252 B2
(45) Date of Patent: Mar. 15, 2016

(54) LACTIC ACID BACTERIUM HAVING HIGH OXALIC ACID DECOMPOSITION ABILITY

(75) Inventors: Daisuke Ochi, Kanagawa (JP); Hiroshi Tsuboi, Kanagawa (JP)

(73) Assignee: Meiji Co., Ltd., Tokyo (JP)

( * ) Notice: Subject to any disclaimer, the term of this patent is extended or adjusted under 35 U.S.C. 154(b) by 604 days.

(21) Appl. No.: 13/119,382

(22) PCT Filed: Sep. 29, 2009

(86) PCT No.: PCT/JP2009/066881
§ 371 (c)(1),
(2), (4) Date: Jun. 7, 2011

(87) PCT Pub. No.: WO2010/038714
PCT Pub. Date: Apr. 8, 2010

(65) Prior Publication Data
US 2011/0236360 A1 Sep. 29, 2011

(30) Foreign Application Priority Data

Sep. 30, 2008 (JP) ................................ 2008-254975

(51) Int. Cl.
*C12N 1/20* (2006.01)
*A61K 35/74* (2015.01)
*A23L 1/30* (2006.01)
*C12R 1/225* (2006.01)

(52) U.S. Cl.
CPC .............. *A61K 35/74* (2013.01); *A23L 1/3014* (2013.01); *C12R 1/225* (2013.01); *A23V 2002/00* (2013.01); *A23Y 2220/37* (2013.01)

(58) Field of Classification Search
None
See application file for complete search history.

(56) References Cited

U.S. PATENT DOCUMENTS

| 6,562,336 B2 | 5/2003 | De Simone |
| 2005/0158293 A1 | 7/2005 | Boileau et al. |

FOREIGN PATENT DOCUMENTS

| JP | 2003-500451 A | 1/2003 |
| JP | 2006-262818 A | 10/2006 |
| JP | 2007-513639 A | 5/2007 |
| JP | 2008-517628 A | 5/2008 |
| RU | 2139346 C1 | 10/1999 |
| WO | WO 00/72855 A2 | 12/2000 |
| WO | WO 2005/060708 A2 | 7/2005 |
| WO | WO 2006/047680 A2 | 5/2006 |
| WO | WO 2007/070677 A2 | 6/2007 |

OTHER PUBLICATIONS

Azcarate-Peril, M.A. et al., "Transcriptional and Functional Analysis of Oxalyl-Coenzyme A (CoA) Decarboxylase and Formyl-CoA Transferase Genes from Lactobacillus Acidophilus," Applied and Environmental Microbiology, Mar. 2006, pp. 1891-1899, vol. 72, No. 3.
Duncan, S.H. et al., "*Oxalobacter formigenes* and Its Potential Role in Human Health," Applied and Environmental Microbiology, Aug. 2002, pp. 3841-3847, vol. 68, No. 8.
Itani, "Experimental Small Animal Model of Renal Calculi (Stone) Formation," 1987, Kidney and Dialysis, pp. 503-508 (13 pages incl. translation).
International Search Report, International Application No. PCT/JP2009/066881, Dec. 14, 2009, 2 pages.
Kamikawa, S. et al., "Autoradiographic Studies of Oxalate Distribution in Rat Kidney," 1996, pp. 900-908.
Lewanika, T.R. et al., "*Lactobacillus gasseri* Gasser AM63$^T$ Degrades Oxalate in a Multistage Continuous Culture Simulator of the Human Colonic Microbiota," FEMS Microbiology Ecology, 2007, pp. 110-120, vol. 61.
Ogawa, "Method of Examining Metabolic Systems Associated with Calculi (Stone)," Japanese Journal of Clinical Urology, Jun. 1991, pp. 47-49 (8 pages incl. translation), vol. 45, No. 6.
Reid, G., "Probiotics and Prebiotics—Progress and Challenges," International Dairy Journal, 2008, pp. 969-975, vol. 18.
Turroni, S. et al., "Oxalate Consumption by Lactobacilli: Evaluation of Oxalyl-CoA Decarboxylase and Formyl-CoA Transferase Activity in *Lactobacillus acidophilus*," Journal of Applied Microbiology, 2007, pp. 1600-1609, vol. 103, No. 5.
"Urolithiasis: Guidelines for Prevention of Recurrence," 2005, Japan Council for Quality Health Care, 2004, 6 pages, [Online] Retrieved from the Internet<URL:http://minds.jcqhc.or.jp/stc/0022/1/0022_G0000058_0062.html>.
Yasui, T. et al., Prevalence and Epidemiological Characteristics of Urolithiasis in Japan: National Trends Between 1965 and 2005, Urology, 2008, pp. 209-213, vol. 71, No. 2.
Campieri, C. et al., "Reduction of Oxaluria After an Oral Course of Lactic Acid Bacteria at High Concentration," Kidney International, 2001, pp. 1097-1105, vol. 60.

*Primary Examiner* — Irene Marx
(74) *Attorney, Agent, or Firm* — Fenwick & West LLP

(57) ABSTRACT

The present invention provides lactic acid bacteria having oxalic acid-degrading activity several times higher than those of conventionally known lactic acid bacteria having an oxalic acid-degrading activity, and uses thereof. Lactic acid bacteria capable of degrading a large amount of oxalic acid were screened from 132 strains of *Lactobacillus* lactic acid bacteria that have been independently isolated from feces and gastric juices of human adults. As a result, lactic acid bacteria having an oxalic acid degradation rate of 50% or more when cultured at 37° C. for 72 hours in a culture medium containing 10 mM oxalic acid at pH 6.5 at the start of culture were discovered.

2 Claims, 1 Drawing Sheet

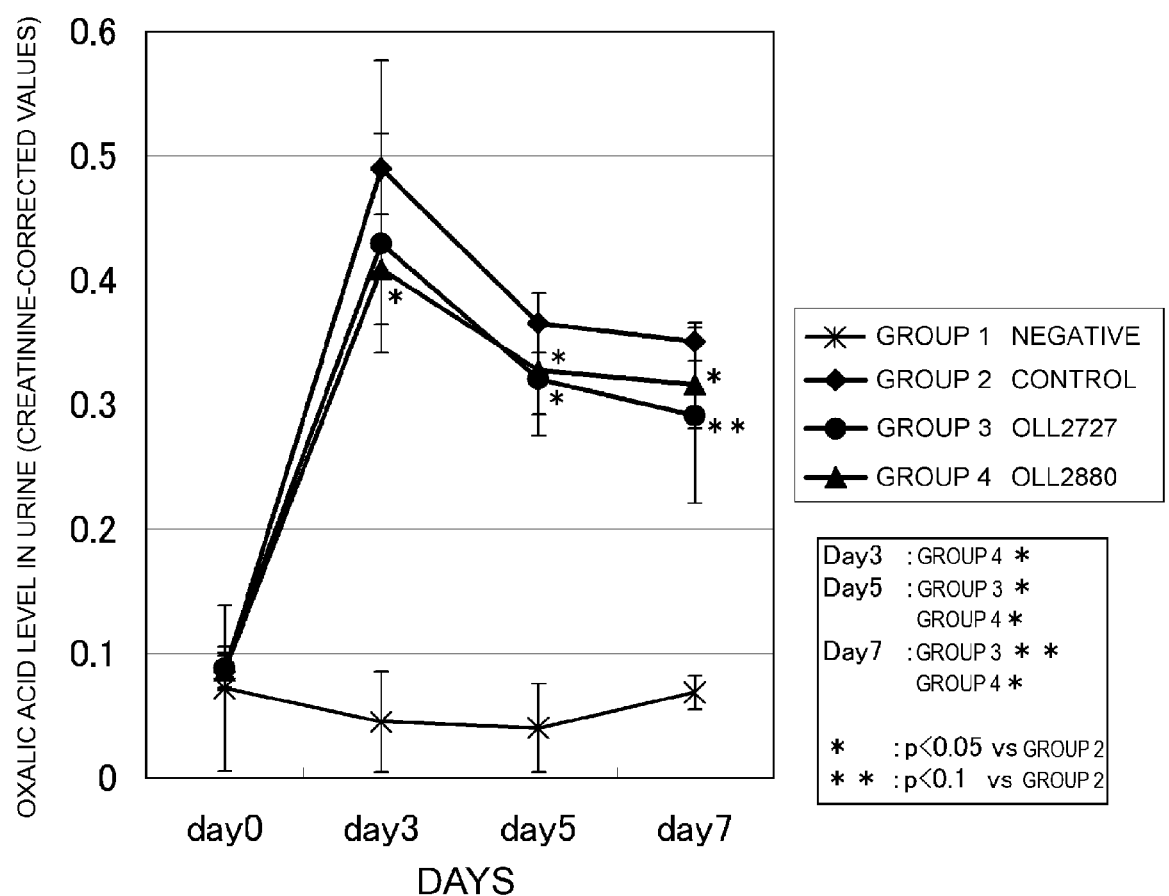

LACTIC ACID BACTERIUM HAVING HIGH OXALIC ACID DECOMPOSITION ABILITY

TECHNICAL FIELD

The present invention relates to lactic acid bacteria that have high oxalic acid-degrading ability and uses thereof.

BACKGROUND ART

Urinary calculi often accompany severe abdominal pain, and this pain suddenly occurs as a result of stimulation from the calculi passing through the urinary tract, or such. Renal calculi have no symptoms in many cases, but when asymptomatic calculi are left as they are, they may cause renal impairment or bacterial infection and such due to hydronephrosis.

In recent years, as a result of the development of extracorporeal shock wave lithotripsy (ESWL), urinary calculi treatment has reached a remarkable development, and the therapeutic outcome has dramatically improved. However, the yearly incidence of urinary calculi in Japan in 2005 was 134 (per 100,000 population), and it is increasing yearly. Also, the recurrence rate is high (Non-patent Document 1). Therefore, from now on, it may become important to focus on prevention, and not simply on treatment of naturally removing the calculi or crushing the calculi (Non-patent Document 2).

However, intake of water, improvement of dietary habits, and medical treatment are regarded as the only effective means for preventing calculi, and examples of improvement of dietary habits include restriction of excessive animal protein intake, specific amount (600 to 800 mg/day) of calcium intake, restriction of excessive intake of salt and lipids, and intake of citric acid. Furthermore, it is said that the formation of calcium oxalate calculi can be prevented by avoiding the intake of oxalic acid (Non-patent document 3).

In Japan, calcium-containing calculi account for 85% or more of renal urolithiasis, and 75% of the calcium-containing calculi are calcium oxalate calculi (Non-patent Document 4). Hypercalciuria, hyperoxaluria, and such may be a cause of calcium oxalate calculi (Non-patent Document 5).

Currently, it is common to use those promote calculi elimination such as chorei-to as the major therapeutic method for urinary calculi, but there are no proven pharmaceutical agents that are used for the purpose of preventing calculi formation.

For prevention using microorganisms, it has been reported that a bacterium present in the intestinal tract called *Oxalobacter formigenes* may reduce the risk of recurrence of renal calculi (Non-patent Document 6), and it is highly possible to prevent renal calculi by using enterobacteria having the ability to degrade oxalic acid. Lactic acid bacteria have been reported to have a number of physiological effects such as intestine function-regulating effect and antiallergic property, and several species are reported to have an oxalic acid degradation ability (Patent Document 1). Furthermore, it is known that oxalic acid degradation ability can be increased to a certain degree, in mutant strains with increased oxalic acid degradation ability, or under conditions in which oxalic acid degradation ability is induced by subculturing in a culture medium containing oxalic acid in advance to increase the oxalic acid degradation ability (Patent Document 2 and Non-patent Document 7).

Information on prior art documents relating to the present invention is shown below.

PRIOR ART DOCUMENTS

Patent Documents

[Patent Document 1] Japanese Patent Application Kohyo Publication No. (JP-A) 2003-500451 (unexamined Japanese national phase publication corresponding to a non-Japanese international publication)
[Patent Document 2] JP-A (Kohyo) 2008-517628

Non-Patent Documents

[Non-patent Document 1] Prevalence and epidemiological characteristics of urolithiasis in Japan: national trends between 1965 and 2005. Urology 71: 209-213, 2008
[Non-patent Document 2] Nihon Hinyokika Gakkai Zasshi (Journal of the Japanese Urological Association) Vol. 87, No. 6, pp. 900-908
[Non-patent Document 3] "Saihatsu Yobo Gaidorain (Guidelines for Prevention of Recurrence)" Nyoro Kesseki-sho Shinryo Gaidorain (Guideline for Medical Care of Urinary Caciculi), revised edition (2004 edition)
[Non-patent Document 4] Jin to Toseki (Kidney and Dialysis) 1987 Supplementary Volume
[Non-patent Document 5] "Methods for testing the metabolic system relating to calculi" Rinsho Hinyokika (Clinical Urology): Ogawa, Y., 45; 47, 1991
[Non-patent Document 6] Duncan, et al., Appl. Environ. Microbiol. 2002 August; 68(8): 3841-7
[Non-patent Document 7] Transcriptional and Functional Analysis of Oxalyl-Coenzyme A (CoA) Decarboxylase and Formyl-CoA Transferase Genes from *Lactobacillus acidophilus*. Applied and Environmental Microbiology. 2006 March; 72(3): 1891-1899

DISCLOSURE OF THE INVENTION

Problems to be Solved by the Invention

The present invention was achieved in view of the above circumstances. An objective of the present invention is to provide lactic acid bacteria having high oxalic acid degradation ability, processed materials of the lactic acid bacteria, methods for degrading oxalic acid or oxalate compounds, and methods for producing compositions with reduced oxalic acid or oxalate compounds. Another objective is to provide compositions comprising the lactic acid bacteria or processed materials thereof, or agents for degrading oxalic acid or oxalate compounds.

Means for Solving the Problems

As a result of dedicated research to solve the above-mentioned objectives, the present inventors isolated lactic acid bacteria having an oxalic acid-degrading activity several times higher than those of known lactic acid bacteria with oxalic acid-degrading activity, and thereby completed the present invention. Specifically, they carried out dedicated selection to obtain lactic acid bacteria that are capable of degrading a large quantity of oxalic acid. Lactic acid bacteria that are capable of degrading a large quantity of oxalic acid were screened from 132 strains of *Lactobacillus* lactic acid bacteria that have been independently isolated from feces and gastric juices of human adults. As a result, the present inventors found lactic acid bacteria that have an oxalic acid degradation rate of 50% or more when cultured at 37° C. for 72 hours in a culture medium containing 10 mM oxalic acid at pH 6.5 at the start of culture, and thereby completed the present invention.

More specifically, the present invention provides the following:

[1] a lactic acid bacterium belonging to the genus *Lactobacillus*, having an oxalic acid degradation rate of 50% or more when cultured at 37° C. for 72 hours in a culture medium containing 10 mM oxalic acid at pH 6.5 at the start of culture;
[2] the lactic acid bacterium of [1], wherein the lactic acid bacterium belonging to the genus *Lactobacillus* is the *Lactobacillus gasseri* species or the *Lactobacillus amylovorus* species;
[3] a lactic acid bacterium selected from the group consisting of (a) to (d) below:
(a) the *Lactobacillus gasseri* OLL203195 strain, which is a lactic acid bacterium deposited under Accession No. FERM BP-11005;
(b) the *Lactobacillus amylovorus* OLL2741 strain, which is a lactic acid bacterium deposited under Accession No. FERM BP-11007;
(c) the *Lactobacillus amylovorus* OLL2880 strain, which is a lactic acid bacterium deposited under Accession No. FERM BP-11006; and
(d) the *Lactobacillus gasseri* OLL2727 strain, which is a lactic acid bacterium deposited under Accession No. FERM BP-11004;
[4] a processed material of the lactic acid bacterium of any one of [1] to [3];
[5] a composition comprising the lactic acid bacterium of [1], [2], or [3], or the processed material of [4];
[6] the composition of [5] for treating and/or preventing renal/urinary calculus;
[7] the composition of [5] for treating and/or preventing anemia;
[8] the composition of [5] for treating and/or preventing osteoporosis;
[9] the composition of any one of [5] to [8], which is a pharmaceutical composition;
[10] the composition of any one of [5] to [8], which is a food composition;
[11] an agent for degrading oxalic acid or an oxalate compound, comprising the lactic acid bacterium of [1], [2], or [3], or the processed material of [4];
[12] a method for degrading oxalic acid or an oxalate compound, wherein the method comprises the step of contacting oxalic acid or an oxalate compound with the lactic acid bacterium of [1], [2], or [3], or the processed material of [4];
[13] a method for producing a composition with reduced level of oxalic acid or oxalate compound, wherein the method comprises the step of contacting a composition comprising the oxalic acid or the oxalate compound with the lactic acid bacterium of [1], [2], or [3], or the processed material of [4];
[14-1] a method for treating and/or preventing renal/urinary calculus, which comprises the step of administering the lactic acid bacterium of [1], [2], or [3], or the processed material of [4] to a subject;
[14-2] a method for treating and/or preventing renal/urinary calculus, which comprises the step of administering the composition of [5] to a subject;
[15-1] a method for treating and/or preventing anemia, which comprises the step of administering the lactic acid bacterium of [1], [2], or [3], or the processed material of [4] to a subject;
[15-2] a method for treating and/or preventing anemia, which comprises the step of administering the composition of [5] to a subject;
[16-1] a method for treating and/or preventing osteoporosis, which comprises the step of administering the lactic acid bacterium of [1], [2], or [3], or the processed material of [4] to a subject;
[16-2] a method for treating and/or preventing osteoporosis, which comprises the step of administering the composition of [5] to a subject;
[17] use of the lactic acid bacterium of [1], [2], or [3], or the processed material of [4] in the production of a pharmaceutical composition for treating and/or preventing renal/urinary calculus;
[18] use of the lactic acid bacterium of [1], [2], or [3], or the processed material of [4] in the production of a pharmaceutical composition for treating and/or preventing anemia;
[19] use of the lactic acid bacterium of [1], [2], or [3], or the processed material of [4] in the production of a pharmaceutical composition for treating and/or preventing osteoporosis;
[20-1] the lactic acid bacterium of [1], [2], or [3], or the processed material of [4] for use in the method for treating and/or preventing renal/urinary calculus;
[20-2] the composition of [5] for use in the method for treating and/or preventing renal/urinary calculus;
[21-1] the lactic acid bacterium of [1], [2], or [3], or the processed material of [4] for use in the method for treating and/or preventing anemia;
[21-2] the composition of [5] for use in the method for treating and/or preventing anemia;
[22-1] the lactic acid bacterium of [1], [2], or [3], or the processed material of [4] for use in the method for treating and/or preventing osteoporosis; and
[22-2] the composition of [5] for use in the method for treating and/or preventing osteoporosis.

BRIEF DESCRIPTION OF THE DRAWINGS

FIG. 1 shows the results obtained by orally administering lactic acid bacteria (genus *Lactobacillus*) with high oxalic acid degradation ability to dietary hyperoxaluria model animals, and measuring the urinary oxalate levels. Significant suppression of the increase in urinary oxalate level (* in the FIGURE) was observed on days 3, 5, and 7 after start of administration in the *L. amylovorus* OLL2880 strain-administered group (Group 4). Significant suppression of the increase in urinary oxalate level was also observed in the *L. gasseri* OLL2727 strain-administered group (Group 3).

MODE FOR CARRYING OUT THE INVENTION

The present invention relates to lactic acid bacteria belonging to the genus *Lactobacillus*, which are characterized by having an oxalic acid degradation rate of 50% or more when cultured at 37° C. for 72 hours in a culture medium containing 10 mM oxalic acid at pH 6.5 at the start of culture (hereinafter referred to as "lactic acid bacteria of the present invention").

The genus *Lactobacillus* is one of the representative genera of lactic acid bacteria, and includes 80 or more species. Examples of species included in *Lactobacillus* include *Lactobacillus delbrueckii* subsp. *burgalicus*, *Lactobacillus delbrueckii* subsp. *lactis*, *Lactobacillus casei*, *Lactobacillus helveticus*, *Lactobacillus acidophilus*, *Lactobacillus crispatus*, *Lactobacillus amylovorus* (hereinafter, it may be referred to as *L. amylovorus*), *Lactobacillus gallinarum*, *Lactobacillus gasseri* (hereinafter, it may be referred to as *L. gasseri*), *Lactobacillus oris*, *Lactobacillus rhamnosus*, *Lactobacillus*

*johnsonii*, *Lactobacillus fermentum*, *Lactobacillus brevis*, and *Lactobacillus plantarum*. The lactic acid bacteria of the genus *Lactobacillus* of the present invention may be any species as long as they are lactic acid bacteria having an oxalic acid degradation rate of 50% or more when cultured at 37° C. for 72 hours in a culture medium containing 10 mM oxalic acid at pH 6.5 at the start of culture, and they are preferably the *Lactobacillus gasseri* species or the *Lactobacillus amylovorus* species. Examples include the *Lactobacillus gasseri* OLL203195 strain, the *Lactobacillus amylovorus* OLL2741 strain, the *Lactobacillus amylovorus* OLL2880 strain, and the *Lactobacillus gasseri* OLL2727 strain isolated by the present inventors.

The lactic acid bacteria of the present invention are lactic acid bacteria that are characterized by having an oxalic acid degradation rate of 50% or more when cultured at 37° C. for 72 hours in a culture medium containing 10 mM oxalic acid at pH 6.5 at the start of culture. The present inventors measured the oxalic acid-degrading activity in a number of lactic acid bacteria, and specifically discovered that lactic acid bacteria named the *Lactobacillus gasseri* OLL203195 strain, the *Lactobacillus amylovorus* OLL2741 strain, the *Lactobacillus amylovorus* OLL2880 strain, or the *Lactobacillus gasseri* OLL2727 strain have an oxalic acid degradation rate of 50% or more when cultured at 37° C. for 72 hours in a culture medium containing 10 mM oxalic acid at pH 6.5 at the start of culture.

Oxalic acid is a dicarboxylic acid and has a molecular weight of 90.03 g/mol. Its CAS Registry No. is 144-62-7. It is included in various types of foods such as vegetables (spinach and bamboo shoot), and contributes to their acrid taste. Furthermore, oxalic acid readily forms salts with minerals, and when the blood oxalate concentration is increased, insoluble calcium salts are formed and they lead to diseases such as urinary calculi.

The phrase "oxalic acid degradation rate of 50% or more when cultured at 37° C. for 72 hours in a culture medium containing 10 mM oxalic acid at pH 6.5 at the start of culture" can be restated as "oxalic acid degradation level per viable bacteria count is $3.0 \times 10^{-9}$ µmol/cfu or more when cultured at 37° C. for four hours in a culture medium containing 5 mM oxalic acid at pH 4 at the start of culture", "having an oxalic acid-degrading activity 17 times or more than that of *L. amylovorus* JCM1126$^T$ when cultured at 37° C. for four hours in a culture medium containing 5 mM oxalic acid at pH 4 at the start of culture", or "oxalic degradation rate is 28% or more when cultured at 37° C. for four hours in a culture medium containing 5 mM oxalic acid at pH 4 at the start of culture". The "oxalic acid degradation rate" can be calculated according to the equation described later in Example 1 and such.

The lactic acid bacteria of the present invention can be separated by known methods. For example, they can be isolated by culturing bacteria obtained from the feces of mammals such as humans, separating the *Lactobacillus* lactic acid bacteria based on the shape, physiological characteristics, and such of cultured bacteria, measuring the oxalic acid-degrading activity, and then selecting the *Lactobacillus* lactic acid bacteria having an oxalic acid degradation rate of 50% or more when cultured at 37° C. for 72 hours in a culture medium containing 10 mM oxalic acid at pH 6.5 at the start of culture. Oxalic acid-degrading activity can be measured by known methods, and as an example, can be measured by the method described in the Examples.

Media that are generally suitable for culturing lactic acid bacilli may be used for culturing the lactic acid bacteria of the present invention, and media comprising carbon sources such as glucose, lactose, galactose, fructose, trehalose, sucrose, mannose, and cellobiose; nitrogen sources such as meat extracts, peptone, yeast extract, casein, and whey proteins; and inorganic nutrients such as magnesium sulfate, iron sulfate, and manganese sulfate can be used. One preferable example includes Lactobacilli MRS Broth (Difco, hereinafter also referred to as MRS media). The culture conditions are not particularly restricted, as long as the growth of intestinal lactic acid bacteria is possible. Preferable conditions include, for example, pH 5.0 to pH 8.0, and temperature of 20° C. to 45° C., and more preferable conditions are anaerobic, pH 5.0 to pH 7.0, and temperature of 30° C. to 40° C.

The present inventors deposited the "*Lactobacillus gasseri* OLL203195 strain" and "*Lactobacillus gasseri* OLL2727 strain" of the present invention with the Patent Organism Depositary of the National Institute of Advanced Industrial Science and Technology. Herein below, the contents specifying the deposit are described.

(1) Name of Depositary institution: International Patent Organism Depositary (IPOD) of the National Institute of Advanced Industrial Science and Technology (AIST)

(2) Contact information: Tsukuba Central 6, 1-1-1 Higashi, Tsukuba, Ibaraki, Japan Postal Code: 305-8566

Telephone Number: 029-861-6029, 6079

(3) Identification display: *Lactobacillus gasseri* OLL203195 (Accession No.: FERM BP-11005; original date of deposition: Sep. 2, 2008)

Identification display: *Lactobacillus gasseri* OLL2727 (Accession No.: FERM BP-11004; original date of deposition: Sep. 2, 2008)

The *Lactobacillus gasseri* OLL203195 strain (Accession No.: FERM BP-11005) and the OLL2727 strain (Accession No.: FERM BP-11004) are Gram-positive bacilli, and their colony morphology on Lactobacilli MRS Agar (Difco) is round, pale yellow, and flat. In terms of physiological characteristics, it shows growth at 45° C. and has the ability to ferment glucose, mannose, fructose, galactose, sucrose, cellobiose, lactose, and trehalose in the form of homolactic acid fermentation. For bacterial cell growth, the pH of the culture medium is preferably maintained at 5.0 to 7.0.

Media that are generally used for culturing lactic acid bacteria are used. More specifically, any media that sufficiently contain the main carbon sources, as well as nitrogen sources, inorganic substances, and other nutrients can be used. Lactose, glucose, sucrose, fructose, starch hydrolysate, molasses, and such may be used as a carbon source according to the assimilation properties of the bacteria used. Organic nitrogen-containing substances such as casein hydrolysate, whey protein hydrolysate, and soy protein hydrolysate can be used as a nitrogen source. Furthermore, meat extract, fish meat extract, yeast extract, and such may be used as growth promoting agents.

It is desirable to carry out culturing under anaerobic conditions, and it may also be carried out under microaerophillic conditions in commonly used liquid static culture and such. For anaerobic culturing, known techniques such as the method of culturing under a carbon dioxide gas layer may be applied, and other methods may also be applied. Generally, the culture temperature is preferably 30 to 40° C., but other temperature conditions are acceptable as long as the temperature allows the bacteria to grow. The pH of the culture medium is preferably maintained at 5.0 to 7.0, but other pH conditions are also acceptable as long as the pH allows the bacteria to grow. Culturing can also be carried out under batch culture conditions. Generally, the culturing time is preferably 10 to 24 hours, but, other culturing times are also acceptable as long as the bacteria can grow.

The present inventors deposited the "*Lactobacillus amylovorus* OLL2741 strain" and "*Lactobacillus amylovorus* OLL2880 strain" of the present invention with the Patent Organism Depositary of the National Institute of Advanced Industrial Science and Technology. Herein below, the contents specifying the deposit are described.

(1) Name of depositary institution: International Patent Organism Depositary (IPOD) of the National Institute of Advanced Industrial Science and Technology (AIST)

(2) Contact information: Tsukuba Central 6, 1-1-1 Higashi, Tsukuba, Ibaraki, Japan Postal Code: 305-8566

Telephone Number: 029-861-6029, 6079

(3) Identification display: *Lactobacillus amylovorus* OLL2741 (Accession No.: FERM BP-11007; original date of deposit: Sep. 2, 2008)

Identification display: *Lactobacillus amylovorus* OLL2880 (Accession No.: FERM BP-11006; original date of deposit: Sep. 2, 2008)

The *Lactobacillus amylovorus* OLL2741 strain (Accession No.: FERM BP-11007) and the strain OLL2880 (Accession No.: FERM BP-11006) are Gram-positive bacilli, and their colony morphology on Lactobacilli MRS Agar (Difco) is round, pale yellow, and flat. In terms of physiological characteristics, it shows growth at 45° C. and has the ability to ferment glucose, mannose, fructose, galactose, sucrose, cellobiose, lactose, and trehalose in the form of homolactic acid fermentation. For bacterial cell growth, the pH of the culture medium is preferably maintained at 5.0 to 7.0.

Media that are generally used for culturing lactic acid bacteria are used. More specifically, any media that sufficiently contain the main carbon sources, as well as nitrogen sources, inorganic substances, and other nutrients can be used. Lactose, glucose, sucrose, fructose, starch hydrolysate, molasses, and such may be used as a carbon source according to the assimilation properties of the bacteria used. Organic nitrogen-containing substances such as casein hydrolysate, whey protein hydrolysate, and soy protein hydrolysate can be used as a nitrogen source. Furthermore, meat extract, fish meat extract, yeast extract, and such may be used as growth promoting agents.

It is desirable to carry out culturing under anaerobic conditions, but it may also be carried out under microaerophillic conditions in commonly used liquid static culture and such. For anaerobic culturing, known techniques such as the method of culturing under a carbon dioxide gas layer may be applied, but other methods may also be applied. Generally, the culture temperature is preferably 30 to 40° C., but other temperature conditions are acceptable as long as the temperature allows the bacteria to grow. The pH of the culture medium is preferably maintained at 5.0 to 7.0, but other pH conditions are also acceptable as long as the pH allows the bacteria to grow. Culturing can also be carried out under batch culture conditions. Generally, the culturing time is preferably 10 to 24 hours, but other culturing times are also acceptable as long as the bacteria can grow.

Furthermore, the present invention relates to processed materials of the lactic acid bacteria of the present invention (hereinafter, referred to as "processed materials of the present invention").

Examples of processed materials used in the present invention include culture, concentrate, paste material, spray-dried material, freeze-dried material, vacuum-dried material, drum-dried material, fluid material, dilution material, and homogenate, but are not limited thereto.

Processed materials of the present invention can be obtained by known methods. For example, cultures or concentrates can be obtained by using the culture supernatant or components of the medium after completion of the culturing of the lactic acid bacteria of the present invention directly, or by concentrating the medium, or such. Furthermore, homogenates can be obtained by homogenizing the lactic acid bacteria or lactic acid bacteria-containing substances of the present invention using a known appropriate device.

The lactic acid bacteria and processed materials of the present invention can be used to degrade oxalic acid or oxalate compounds, or for treatment or prevention of oxalic acid-associated diseases such as renal/urinary calculi, anemia, and osteoporosis.

Furthermore, in the body of subjects who have been administered with the lactic acid bacteria and processed materials of the present invention, absorption of oxalic acid contained in foods can be suppressed by utilizing the oxalic acid-degrading activity of the lactic acid bacteria and processed materials of the present invention.

In the present invention, "subjects" includes organisms that are affected with or at risk of being affected with oxalic acid-associated diseases. Without particular limitation, organisms that are to be administered with the lactic acid bacteria and processed materials of the present invention include animals (for example, humans, livestock animal species, wild animals, and pets).

Furthermore, the present invention relates to compositions comprising a lactic acid bacterium or processed material of the present invention (hereinafter referred to as "compositions of the present invention").

The compositions of the present invention may comprise, for example, medium ingredients, additives suitable for oral ingestion and tubal feeding, and solvent such as water. Additionally they may comprise the later-described pharmaceutically acceptable carriers, carbohydrates, proteins, lipids, vitamins, biologically essential trace metals, flavorings, and such.

The compositions of the present invention can be utilized for degrading oxalic acid or oxalate compounds, or for treating or preventing oxalic acid-associated diseases such as renal/urinary calculi, anemia, and osteoporosis.

The compositions of the present invention include, for example, pharmaceutical compositions (hereinafter, it will be referred to as "pharmaceutical compositions of the present invention").

Pharmaceutical compositions of the present invention may comprise pharmaceutically acceptable carriers in addition to the lactic acid bacteria and processed materials of the present invention, and may be administered orally or parenterally, but the preferred administration method includes oral administration. Examples of pharmaceutically acceptable carriers include surfactants, excipients, coloring agents, flavoring agents, preservatives, stabilizers, buffers, suspending agents, isotonizing agents, binding agents, disintegrants, lubricants, fluidity accelerator, and corrigents, but other commonly used carriers can be used appropriately. Specifically, light anhydrous silicic acid, lactose, crystalline cellulose, mannitol, starch, calcium carmellose, sodium carmellose, hydroxypropylcellulose, hydroxypropylmethylcellulose, polyvinylacetal diethylaminoacetate, polyvinylpyrrolidone, gelatin, middle-chain fatty acid triglyceride, polyoxyethylene hydrogenated castor oil 60, sucrose, carboxymethylcellulose, corn starch, inorganic salts, and such are included.

Various known dosage forms can be used to prepare formulations for oral administration, and such examples include granules, powders, tablets, pills, capsules, liquids, syrups, emulsions, suspensions, and troches. Furthermore, by preparing an enteric-coated formulation by methods well known to those skilled in the art, the lactic acid bacteria or processed materials of the present invention can be transported efficiently to the intestine without being affected by gastric acid.

Pharmaceutical compositions produced using the lactic acid bacteria and processed materials of the present invention are expected to exhibit oxalic acid-degrading activity or preventive and/or therapeutic effects on oxalic acid-associated diseases through the action of these bacteria in the pharmaceutical compositions. Furthermore, the above-mentioned pharmaceutical compositions are expected to exhibit effects of suppressing the absorption of oxalic acid contained in foods in the body of subjects who are administered with the compositions.

Furthermore, compositions of the present invention include, for example, food compositions (hereinafter, referred to as "food compositions of the present invention").

Food compositions of the present invention may include carbohydrates, proteins, lipids, vitamins, biologically essential trace metals (manganese sulfate, zinc sulfate, magnesium chloride, potassium carbonate, and such), flavorings, and other components in addition to the lactic acid bacteria and processed materials of the present invention as long as they do not inhibit the growth of lactic acid bacteria.

Carbohydrates include sugars, processed starch (dextrin, as well as soluble starch, British starch, oxidized starch, starch ester, starch ether, etc.), and dietary fiber.

Examples of proteins include animal and plant proteins such as whole milk powder, skim milk powder, partially-skimmed milk powder, casein, whey powder, whey protein, whey protein concentrate, whey protein isolate, α-casein, β-casein, κ-casein, β-lactoglobulin, α-lactoalbumin, lactoferrin, soybean protein, hen egg protein, meat protein, and hydrolysates thereof; and various types of milk-derived components such as butter, whey mineral, cream, whey, non-protein nitrogen, sialic acid, phospholipids, and lactose.

Examples of lipids include animal oils and fats such as lard and fish oils, as well as their separated oils, hydrogenated oils, and transesterification oils; and vegetable oils such as palm oil, safflower oil, corn oil, rapeseed oil, coconut oil, as well as their separated oils, hydrogenated oils, and transesterification oils.

Examples of vitamins include vitamin A, carotenes, B-complex vitamins, vitamin C, vitamin D family, vitamin E, vitamin K family, vitamin P, vitamin Q, niacin, nicotinic acid, pantothenic acid, biotin, inositol, choline, and folic acid. Examples of minerals include calcium, potassium, magnesium, sodium, copper, iron, manganese, zinc, and selenium.

Food compositions of the present invention are not limited in terms of their category or type, and may be functional food, specified health food, food for specified use, food with nutrient function claims, health food, nursing care food, confectionery, lactic acid bacteria beverage, dairy products such as cheese or yogurt, seasonings, or such. The dietary products are also not limited in their forms, and may take the form of any dietary products that can be commonly distributed such as solid, liquid, fluid diet, jelly, tablets, granules, or capsules, and may be added to various foods (milk, soft drink, fermented milk, yogurt, cheese, bread, biscuit, cracker, pizza crust, formula milk, liquid diet, food for the sick, nutritional food, frozen food, processed food, other commercially available foods, and such). The above-mentioned dietary products can be manufactured using ordinary methods by those skilled in the art.

The lactic acid bacteria or processed materials of the present invention can be processed into common dietary products comprising dairy products/fermented milk as described above, and used as starters for producing dairy products/fermented milk such as yogurt and cheese. When they are used as starters, other microorganisms may be admixed as long as they do not interfere with the manufacturing of dairy products or the inhabitation/proliferation of the lactic acid bacteria of the present invention. For example, they may be admixed with *Lactobacillus delbruekii* subsp. *bulgaricus, Streptococcus thermophilus*, or *Lactobacillus acidophilus* which are major bacterial species of lactic acid bacteria in yogurt, and additionally, they may be admixed with bacterial species generally used for yogurt or cheese and made into starters. Dairy products and fermented milk can be manufactured using the above-mentioned starters by ordinary methods. For example, plain yogurt can be manufactured by admixing the above-mentioned starter with cooled milk or dairy products that have been subjected to heating, mixing, homogenization, sterilization treatment, followed by fermentation and cooling.

Furthermore, the present invention relates to uses of the lactic acid bacteria and processed materials of the present invention.

Examples of the uses include agents for degrading oxalic acid or oxalate compounds, which comprise the lactic acid bacteria or processed materials of the present invention. Such agents for degradation degrade oxalic acid and oxalate compounds.

Such agents for degradation may include in addition to the lactic acid bacteria or processed materials of the present invention, the above-mentioned pharmaceutically acceptable carriers, the above-mentioned carbohydrates, proteins, lipids, vitamins, biologically essential trace metals (manganese sulfate, zinc sulfate, magnesium chloride, potassium carbonate, and such), flavorings, and other components. Furthermore, the dosage forms of the agents for degrading oxalic acid include, for example, the above-mentioned dosage forms.

Furthermore, the degradation agents can be rephrased as "methods for degrading oxalic acid or oxalate compounds, which comprise the step of contacting oxalic acid or oxalate compounds with lactic acid bacteria or a processed material of the present invention".

The above-mentioned step enables efficient degradation of oxalic acid or oxalate compounds. The above-mentioned step is preferably carried out under conditions in which the lactic acid bacteria of the present invention can survive, or conditions in which the lactic acid bacteria of the present invention can ferment.

Furthermore, examples of uses include methods for treating and/or preventing renal/urinary calculi, anemia, and osteoporosis, which comprise the step of administering the lactic acid bacteria or processed materials of the present invention to subjects.

The above-mentioned "subject" refers to organisms to which the lactic acid bacteria or processed materials of the present invention are administered, a part in the body of such organisms, or a part resected or eliminated from such organisms. The organisms are not particularly limited, and include animals (such as humans, livestock animal species, and wild animals).

In the present invention, "administration" includes oral and parenteral administrations. Examples include oral administration, tubal administration, and enteral administration.

Oral administration includes administration in the form of an oral agent, and dosage forms such as granules, powders, tablets, capsules, liquids, emulsions, or suspensions can be selected as the oral agent.

Parenteral administration includes administration in the form of an injection. Furthermore, the lactic acid bacteria or processed materials of the present invention can be administered locally to the region to be treated. For example, they can be administered by using catheters or local injection during surgery.

Furthermore, compositions with reduced oxalic acid or oxalate compounds can be produced by utilizing the oxalic acid-degrading activity of the lactic acid bacteria and processed materials of the present invention. The methods for producing compositions with reduced oxalic acid or oxalate compounds of the present invention comprise the step of contacting compositions comprising oxalic acid or oxalate compounds with the lactic acid bacteria or processed materials of the present invention. This step enables efficient reduction of the amount of oxalic acid or oxalate compound contained in the compositions. Herein, "reduced oxalic acid or oxalate compound" means that the amount of oxalic acid or oxalate compound in the above-mentioned compositions containing oxalic acid or oxalate compound after the above-mentioned step is less than that before the above-mentioned step. The oxalic acid or oxalate compound can be said to be reduced, for example, when the amount of oxalic acid or oxalate compound after the above-mentioned step is less than that before the above-mentioned step by 10% or more, 20% or more, 30% or more, 40% or more, 50% or more, 60% or more, 70% or more, 80% or more, or 90% or more. Furthermore, the oxalic acid or oxalate compound can also be said to be reduced when the compositions do not contain oxalic acid or oxalate compound at all after the above-mentioned steps.

Examples of the above-mentioned "oxalate compound" include oxalate compounds such as metal oxalates, ammonium oxalate salt, and amine salt of oxalic acid, or oxalate contained in plants such as vegetables. More specifically, examples include organic salts or inorganic salts (calcium salt, magnesium salt, sodium salt, sodium hydrogen oxalate, or potassium salt) of oxalic acid, iron oxalate, and oxalic acid hydrate. Furthermore, "oxalate compounds" can be described as "oxalic acid source" or "compounds that produce oxalate ions when dissolved in water.

All prior art references cited herein are incorporated by reference into this description.

EXAMPLES

Herein below, the present invention will be specifically described with reference to the Examples, but it is not to be construed as being limited thereto.
<Standard Strains>
L. gasseri JCM1131$^T$
L. amylovorus JCM1126$^T$ Example 1

For the lactic acid bacteria samples used below, lactic acid bacterial strains held by Meiji Dairies Corporation and lactic acid bacterial strains obtained from the Japan Collection of Microorganisms (JCM) RIKEN BioResource Center were used. OLL in the bacterial strain name indicates bacterial strains held by Meiji Dairies Corporation. JCM in the bacterial strain name indicates bacterial strains held by the Japan Collection of Microorganisms (JCM) RIKEN BioResource Center.

The bacterial cells of each of the lactic acid bacteria samples were dispersed in a sterilized 10% (w/v) skim milk medium (Meiji Dairies Corporation), and stored at −80° C. in a deep freezer until use.

The following method was used to perform primary screening of bacteria having degradation activity against oxalic acid.

A total of 41 bacterial strains which include several strains from each species of the 27 species of lactic acid bacteria held by Meiji Dairies Corporation were used.

Each bacterial strain was placed in a sealed container with an oxygen-absorbing/carbon dioxide gas-producing agent "AnaeroPack-Kenki" (manufactured by Mitsubishi Gas Chemical Co., Inc.) and anaerobically cultured (37° C., 16 hours) in an MRS medium (Difco, Detroit, Mich., USA). Next, OD600 of the obtained culture solution was measured, and the OD600 was adjusted to 1. Thereafter, 5 μL of the OD600-adjusted culture solution was added to 5 mL of a medium produced by mixing equal amounts of an MRS medium (Difco, Detroit, Mich., USA) with 20 mM ammonium oxalate solution (pH 6.5, containing 50 μmol of oxalic acid), and the obtained bacterial cell suspension solution was placed into a sealed container with "Anaero Pack-Kenki" and statically cultured at 37° C. for 72 hours.

The obtained culture solution was diluted ten times and OD600 was measured using an absorption spectrometer.

1 mL of the obtained culture solution was centrifuged at 15,000 rpm for one minute at 4° C., and 50 μL of 30 mM crotonic acid solution was added as an internal standard solution to 500 μL of the supernatant. Then, proteins were removed using the Carrez reagent (Carrez I solution (53.5 g of $ZnSO_4 \cdot 7H_2O$ in 100 mL of distilled water) and Carrez II solution (17.2 g of $K_4[Fe(CN)_6] \cdot 3H_2O$ in 100 mL of distilled water), and this was centrifuged at 10,000 rpm for three minutes at 4° C. The supernatant was collected using a 0.22 μm filter. Thereafter, this solution was subjected to HPLC. For all the oxalic acid measurements in the solutions below, the above-mentioned method was used, and in all experiments, HPLC was performed under the following conditions.

<Analytical Instrument>

High performance liquid chromatography: SCL-10A (manufactured by Shimadzu Corporation)

<Conditions for Analysis>

Column: polymer column for organic acid analysis, Tokyo Chemical Industry Co., Ltd./TRANSGENOMIC ICSep ICE-ORH-801 6.5 mm I.D.×300 mm Guard Kit: Guard column cartridge for organic acid analysis ICSep ICE-ORH-801 4.0 mm I.D.×20 mm Detector: Electrical conductance detector (Shimadzu CDD-10A)

Mobile phase: aqueous 5 mM p-toluene sulfonic acid solution

Reaction solution: aqueous 5 mM p-toluene sulfonic acid-100 μM EDTA (2Na)/20 mM Bis-Tris solution Oven temperature: 50° C.

Flow rate: 0.5 mL/min (both mobile phase and reaction solution)

Amount of sample: 10 μL

Oxalic acid and crotonic acid were determined from the HPLC retention time. Each compound was quantified based on the peak area values in the HPLC chart. Furthermore, the degradation rate of oxalic acid was calculated according to the following equation:

$$\text{Degradation rate (\%)} = \{(a-X)/a\} * 100$$

a: oxalic acid concentration in the medium before the reaction
X: oxalic acid concentration in the culture supernatant after the reaction

TABLE 1

| BACTERIAL STRAIN | STRAIN | DEGRADATION RATE (%) | OD600 0 HOUR AFTER CULTURE | OD600 72 HOURS AFTER CULTURE |
|---|---|---|---|---|
| L. gasseri | OLL203915 | 67.2 | 0.03 | 3.01 |
| L. amylovorus | OLL2741 | 57.3 | 0.02 | 3.77 |
| L. amylovorus | OLL2880 | 56.1 | 0.03 | 4.18 |
| L. gasseri | OLL2727 | 56.7 | 0.05 | 2.78 |

The assay was performed by about the same technique described in Example 1 of JP-A (Kohyo) 2003-500451. As a result, while the maximum value of the degradation rate was 11.79% in Example 1 of JP-A (Kohyo) 2003-500451, this assay shows that bacterial strains with extremely high degradation rates were present in *L. gasseri*, *L. amylovorus*, and the *Bifidobacterium adolescentis* species. Furthermore, the degradation rate was 56% or more in the above-mentioned four strains. That is, the four bacterial strains of Table 1 discovered in the present invention were revealed to have oxalic acid-degrading activity approximately five times (4.86 times) higher than that of the bacterial strain discovered in JP-A (Kohyo) 2003-500451.

Example 2

The following examinations were carried out using the *L. gasseri* OLL2727 strain which showed high activity in Example 1.

The bacterial strain was placed in a sealed container with an oxygen-absorbing/carbon dioxide gas-producing agent "AnaeroPack-Kenki" (manufactured by Mitsubishi Gas Chemical Co., Inc.) and anaerobically cultured (37° C., 16 hours) in MRS medium (Difco, Detroit, Mich., USA). Next, OD600 of the obtained culture medium was measured, and the OD600 was adjusted to 5. Then, 5 mL of the culture medium whose OD600 was adjusted to 5 was centrifuged at 3,000 rpm for ten minutes at room temperature to collect the bacterial cells. The obtained bacterial cells were washed with 0.8% physiological saline solution, and this was again centrifuged at 3,000 rpm for ten minutes at room temperature to collect the bacterial cells.

Water was added to 42.65 g of 2-(N-morpholino)ethanesulfonic acid (Nacalai Tesque), 5 g of glucose (Wako), 0.9 g of NaCl (Wako), 0.4 g of $KH_2PO_4$ (Wako), 0.45 g of $(NH_4)_2SO_4$ (Wako), 0.09 g of $MgSO_4.7H_2O$ (Wako), 0.05 g of $CaCl_2$ (Kanto Chemical), 0.4 g of $K_2HPO_4$ (Wako), and 0.5 g of L-cysteine hydrochloride monohydrate (Wako) to adjust the volume to 1 L, and this was used as medium B. Equal amounts of the medium B and 10 mM ammonium oxalate solution were added, and the pH was adjusted to 4 and 6 using a small amount of hydrochloric acid or sodium hydroxide. This was sterilized by filtration with a 0.45 µm filter, and the resulting solution was used as medium A.

5 mL of medium A (pH=4 and 6) was added to the obtained bacterial cells, and the bacterial cell suspension obtained as a result was placed in a sealed container with "AnaeroPack-Kenki" and statically cultured at 37° C. for six hours. The amount and degradation rate of oxalic acid in the obtained culture solution were measured and calculated according to the method described in Example 1.

TABLE 2

| | BACTERIAL STRAIN OLL2727 | |
|---|---|---|
| pH | OXALIC ACID DEGRADATION LEVEL (mM) | DEGRADATION RATE (%) |
| 6 | 0.23 | 5.1 |
| 4 | 3.01 | 63.5 |

The results showed that the activity is higher at pH 4.0 than at pH 6.0. This indicates the possibility that the bacterial strain will survive and exhibit oxalic acid-degrading activity in the stomach which has a low pH. That is, it can be said to be a strain having oxalic acid-degrading activity in the stomach. Although the activity is lower at pH 6 than at pH 4, the bacterial strain survives and has oxalic acid-degrading activity. The pH in the intestines is normally around 6.5; therefore, this indicates the possibility that the bacterial strain survives also in the intestines and exhibits oxalic acid-degrading activity. Furthermore, as lactic acid bacteria in the intestines produce lactic acid, the pH may be lowered locally in the intestines and oxalic acid degradation may be expected not only in the stomach where the pH is low, but also in the intestines.

Example 3

Accordingly, the following experiment was carried out using 132 strains of human-derived *L. acidophilus* group held by Meiji Dairies Corporation to which *L. gasseri* and *L. amylovorus* belong.

The oxalic acid-degrading activity of the microorganisms of the present invention was measured and evaluated by the following method.

Each bacterial strain was placed in a sealed container with an oxygen-absorbing agent ("AnaeroPack-Kenki" (manufactured by Mitsubishi Gas Co.)) and anaerobically cultured (37° C., 16 hours) in MRS medium (Difco, Detroit, Mich., USA). Next, OD600 of the obtained culture solution was measured, and the OD600 was adjusted to 5. Thereafter, 5 mL of the culture medium whose OD600 was adjusted to 5 was centrifuged at 3,000 rpm for ten minutes at room temperature to collect the bacterial cells. The obtained bacterial cells were washed with 0.8% physiological saline solution, and this was again centrifuged at 3,000 rpm for ten minutes at room temperature to collect the bacterial cells.

5 mL of medium A (pH 4, containing 25 µmol of oxalic acid) used in Example 2 was added to the obtained bacterial cells, and the bacterial cell suspension obtained as a result was placed in a sealed container with "AnaeroPack-Kenki" and statically cultured at pH 4 at 37° C. for four hours. Next, the amount and degradation rate of oxalic acid in the obtained culture solution were measured and calculated according to the method described in Example 1.

TABLE 3

| BACTERIAL STRAIN | STRAIN | OXALIC ACID DEGRADATION LEVEL (mM) | VIABLE BACTERIAL CELL COUNT (cfu/ml) | DEGRADATION LEVEL PER VIABLE BACTERIAL CELL COUNT (μmol/cfu) | DEGRADATION LEVEL PER THE VIABLE BACTERIAL CELL COUNT/DEGRADATION LEVEL PER VIABLE STANDARD BACTERIAL CELL COUNT | DEGRADATION RATE (%) |
|---|---|---|---|---|---|---|
| L. gasseri | 203195 | 2.19 | $4.8 \times 10^8$ | $4.6 \times 10^{-9}$ | 13.1 | 43.8 |
| L. amylovorus | 2741 | 1.74 | $4.4 \times 10^8$ | $4.0 \times 10^{-9}$ | 20.0 | 34.8 |
| L. amylovorus | 2880 | 1.82 | $5.0 \times 10^8$ | $3.6 \times 10^{-9}$ | 18.0 | 36.6 |
| L. gasseri | 2727 | 1.40 | $4.0 \times 10^8$ | $3.5 \times 10^{-9}$ | 10.0 | 28.1 |
| L. gasseri | JCM1131T | 0.31 | $8.8 \times 10^8$ | $3.5 \times 10^{-10}$ | | 6.2 |
| L. amylovorus | JCM1126T | 0.10 | $5.0 \times 10^8$ | $2.0 \times 10^{-10}$ | | 2.0 |

It was possible to obtain strains with high oxalic acid-degrading activity in which the level of oxalic acid degradation per viable bacterial cell count is 10 to 20 times or higher than that of the standard strain for each of the species.

Of the 132 strains screened, 42 strains had zero oxalic acid-degrading activity, 34 strains had an activity of 0.1 mM or less, 49 strains had an activity of 1 mM or less, and seven strains had an activity of 1 mM or more, and there were very few strains with high oxalic acid-degrading activity. It is considered advantageous to have fast, high oxalic acid-degrading activity when oxalic acid degradation effects are expected in the body of animals.

Since human-derived strains were used in this experiment, these human-derived strains are highly likely to be able to pass through the human digestive tract alive, and may be used as probiotics. They are bacteria that degrade large amounts of oxalic acid within a short period of four hours at pH 4. Thus, if large amounts of oxalic acid can be degraded in the stomach, the amount of oxalic acid taken downstream to the small intestine will decrease, and these bacteria will be able to reduce the urinary oxalate levels more effectively than the oxalic acid-degrading bacteria in the intestines. Furthermore, although the pH in the intestines is normally around 6.5, the lactic acid produced by lactic acid bacteria in the intestines may result in low local pH in the intestines, and oxalic acid degradation may be possible not only in the stomach where the pH is low, but also in the intestines.

Thus, the four bacterial strains, *Lactobacillus gasseri* OLL203195, *Lactobacillus amylovorus* OLL2741, *Lactobacillus amylovorus* OLL2880, and *Lactobacillus gasseri* OLL2727, were found to have oxalic acid-degrading activity approximately five times (4.86 times) higher than that of the bacterial strains discovered in JP-A (Kohyo) 2003-500451.

Example 4

In Vivo Experimental Method on the Urinary Oxalate-Reducing Effect of Lactic Acid Bacteria Dietary hyperoxaluria model animals were prepared, and the effects of the microorganisms (lactic acid bacteria) on the animals' urinary oxalate levels were examined. Specifically, the above-mentioned method prepares mixed water containing 0.075 weight % of oxalic acid dihydrate, allows rats to ingest this water, and compares the post-ingestion urinary oxalate levels with those of the negative group and the control group.

[Materials and Experimental Procedure]
[Microorganisms]

Two strains *Lactobacillus gasseri* OLL2727 (hereinafter "*Lactobacillus*" will be abbreviated in some cases as "*L.*") and *L. amylovorus* 2880 which were assessed to have high oxalic acid-degrading ability in the in vitro experiment were used. Bacterial cell suspension solutions were prepared from each type of lactic acid bacteria in the same manner as in the in vitro experiments. The bacterial cell suspension solutions were orally administered to the rats at $1\times10^{10}$ CFU/10 mL/kg. The solution used for the bacterial cell suspension solutions was prepared by adding water to 2.5 g of glucose (Wako), 0.45 g of NaCl (Wako), 0.2 g of $KH_2PO_4$ (Wako), 0.2 g of $(NH_4)_2SO_4$ (Wako), 0.045 g of $MgSO_4\cdot 7H_2O$ (Wako), 0.025 g of $CaCl_2$ (Kanto Chemical), 0.2 g of $K_2HPO_4$ (Wako), and 0.25 g of L-cysteine hydrochloride monohydrate (Wako) to adjust the volume to 1 L (Hereinafter, this solution is called solution X).

[Experimental Animals]

Rats (Wistar SPF, male, 7 weeks old) were used. Plastic cages for rats were used for rearing (habituation and testing), and a single rat was housed in each cage. The light-dark cycle was light from 7 a.m. to 7 p.m. (12 hours).

[Preliminary Rearing (Habituation) and Group Division]

Experimental animals went through a one-week preliminary rearing (habituation) after they were brought in. During habituation, the animals were allowed to freely consume AIN-93G (Oriental Yeast Co. Ltd.) with an adjusted calcium content of 50 mg/100 g (hereinafter, this food will be referred to as special AIN-93G) as feed (food) and injection solvent (Otsuka) as drinking water. After preliminary rearing, the rats (seven days after arrival, eight weeks old, Day 0) were placed in a metabolism cage and urine samples were collected for 24 hours (from the morning of Day 6 to the morning of Day 7). The pH of this urine was adjusted to 5 using 2N hydrochloric acid, and to avoid calcium oxalate precipitation, EDTA was added at 0.5 g/L. The level of oxalate in the obtained urine was measured by HPLC according to the methods described in Example 1. Furthermore, urinary creatinine was measured using a creatinine assay kit (LABOASSAY creatinine (Jaffe method) (Wako Pure Chemical Industries)). The method was performed using the microplate method by following the instructions.

Groups were divided such that the urinary oxalate level in each group became equal. A total of four groups with seven rats in each group (only the negative group with three rats) were used in the test: negative group (Group 1), control group (Group 2), and bacterial cell-administered groups (Groups 3 and 4). The names of the groups, feed, water, administered substance (administration dose), number of animals, and such are indicated below.

Negative group (Group 1): "special AIN-93G" as feed, "injection solvent" as water, no administration, three rats Control group (Group 2): "special AIN-93G" as feed, "injection solvent containing oxalic acid dihydrate at 0.075 weight %" as water, "solution X" was administered (10 mL/kg), seven rats Bacterial cell-administered group (Groups 3 and 4): in both groups, "special AIN-93G" as feed, "injection solvent containing oxalic acid dihydrate at 0.075 weight %" as water, rats. The administered bacterial cells and doses for each group are as follows.

In Group 3, "a suspension solution of *L. gasseri* 2727 strain in solution X ($1 \times 10^9$ CFU/mL)" was administered (10 mL/kg); and in Group 4, "a suspension solution of *L. amylovorus* 2880 strain in solution X ($1 \times 10^9$ CFU/mL)" was administered (10 mL/kg).

[Main Breeding (Test)]

The test period was set to be eight days from the day after group division, and each of the "injection solvent" drinking water (negative groups) and "injection solvent containing oxalic acid dihydrate at 0.075 weight %" drinking water (control groups and bacterial cell-administered groups) were freely fed to the rats using a water feeder. The start date of watering the drinking water was set to Day 1, and the subsequent days were counted from this date. $1 \times 10^{10}$ CFU/10 mL/kg of the aforementioned bacterial cell suspension was orally administered by force to the experimental animals of the bacterial cell-administered groups. To the control group, 10 mL/kg of solution X instead of the bacterial cell suspension was orally administered by force.

[Measurement, Examination, and Such]

Observation of the General Status and Measurement of Body Weight

In all cases (all groups), the general status was observed at the time of administration every day from Day 1 to Day 8, and the body weight was measured at a fixed time between 9 a.m. and 10 a.m. on days 0, 3, 5, and 7.

Measurement of Feed Consumption and Water Consumption

In all cases (all groups), feed consumption and water consumption were measured at a fixed time between 9 a.m. and 10 a.m. on Day 3 (set level), Day 5 (residual level, set level), and Day 7 (residual level).

Urine Collection and Biochemical Tests

In all cases (all groups), urine was collected on Days 0, 3, 5, and 7 for 24 hours. The pH of the collected urine was adjusted to 5 using 2N hydrochloric acid, and EDTA was added at 0.5 g/L to avoid calcium oxalate precipitation. The level of oxalate in the obtained urine was measured by HPLC according to the methods described in Example 1. Furthermore, urinary creatinine was measured using a creatinine assay kit (LABOASSAY creatinine (Jaffe method) (Wako Pure Chemical Industries)). The method was performed using the microplate method by following the instructions.

[Statistical Processing]

The results are indicated as the mean±standard deviation, and the control groups were compared with each of the bacterial cell-administered groups. Variance ratios of the numerically converted test values were tested by the F test, Student's t-test was used in the case of equal variance, and Aspin-Welch t-test was used in the case of unequal variance. The statistical analysis of Excel Statistics 2004 was used for statistical processing, and the lowest level of significance was set to 5% on both sides.

[Results]

The results of the general status are shown in Table 4, and the changes in the urinary oxalate level/g-creatinine levels are shown in FIG. 1.

As shown in FIG. 1, significant differences in the reduction of urinary oxalate levels as a result of administration of the lactic acid bacteria were observed in the group administered with *L. amylovorus* OLL 2880 suspended in solution X and the group administered with *L. gasseri* OLL 2727 suspended in solution X. In terms of general status, significant differences were not observed between the control group (Group 2) and the bacterial cell-administered groups (Group 3 and Group 4).

TABLE 4

|  | GROUP 1 | GROUP 2 | GROUP 3 | GROUP 4 |
|---|---|---|---|---|
| AMOUNT OF BODY WEIGHT INCREASE DURING THE TESTING PERIOD (g) | 23.6 ± 7.6 | 14.0 ± 5.4 | 13.9 ± 5.0 | 17.3 ± 5.1 |
| FOOD CONSUMPTION DURING THE TESTING PERIOD (g) | 98.6 ± 17.8 | 92.2 ± 7.0 | 91.6 ± 7.3 | 96.1 ± 5.2 |
| WATER CONSUMPTION DURING THE TESTING PERIOD (g) | 124.3 ± 20.3 | 96.8 ± 9.3 | 98.4 ± 11.4 | 103.3 ± 5.8 |

INDUSTRIAL APPLICABILITY

The present invention provides lactic acid bacteria having oxalic acid-degrading activity several times higher than those of conventionally known lactic acid bacteria having oxalic acid-degrading activity. The lactic acid bacteria, processed materials of the lactic acid bacteria, and compositions comprising the lactic acid bacteria or processed materials are useful for the treatment or prevention of oxalic acid-associated diseases such as renal/urinary calculi, anemia, and osteoporosis; as well as for the production of compositions with reduced amount of oxalic acid or oxalate compounds, or agents for degrading oxalic acid or oxalate compounds; and for methods for degrading oxalic acid or oxalate compounds. Furthermore, since lactic acid bacteria have a long history of being consumed as food, they can be taken safely even if they are administered for long periods of time and in large quantities.

The invention claimed is:

1. A composition comprising a lactic acid bacterium belonging to the genus *Lactobacillus* in an amount effective for treating renal/urinary calculus and a component selected from the group consisting of light anhydrous silicic acid, lactose, crystalline cellulose, mannitol, starch, calcium carmellose, sodium carmellose, hydroxypropylcellulose, hydroxypropylmethylcellulose, polyvinylacetal diethylaminoacetate, polyvinylpyrrolidone, gelatin, polyoxyethylene hydrogenated castor oil 60, sucrose, carboxymethylcellulose, and corn starch, wherein the lactic acid bacterium is the *Lactobacillus gasseri* OLL2727 strain, deposited under Accession No. FERM BP-11004.

2. The composition of claim 1, which is a pharmaceutical composition or food composition.

* * * * *